United States Patent
Cohen et al.

(10) Patent No.: US 8,500,645 B2
(45) Date of Patent: Aug. 6, 2013

(54) LOW POWER ULTRASOUND SYSTEM

(75) Inventors: Benjamin A. Cohen, Phoenix, AZ (US);
Dylan K. Robles, Phoenix, AZ (US);
Shayne Messerly, Kaysville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1253 days.

(21) Appl. No.: 12/100,983

(22) Filed: Apr. 10, 2008

(65) Prior Publication Data

US 2008/0255451 A1    Oct. 16, 2008

Related U.S. Application Data

(60) Provisional application No. 60/922,695, filed on Apr. 10, 2007.

(51) Int. Cl.
*A61B 8/00* (2006.01)
*A61B 8/14* (2006.01)

(52) U.S. Cl.
USPC ............... 600/447; 600/443; 600/459

(58) Field of Classification Search
None
See application file for complete search history.

(56) References Cited

U.S. PATENT DOCUMENTS

| | | |
|---|---|---|
| 3,914,748 A | 10/1975 | Barton et al. |
| 3,918,024 A | 11/1975 | Macovski |
| 4,152,678 A | 5/1979 | Shott et al. |
| 4,159,462 A | 6/1979 | Rocha et al. |
| 4,334,432 A | 6/1982 | Gill |
| 4,413,629 A | 11/1983 | Durley, III |
| 4,542,653 A | 9/1985 | Liu |
| 5,005,419 A | 4/1991 | O'Donnell et al. |
| 5,108,759 A | 4/1992 | Ranney |
| 5,259,386 A | 11/1993 | Sharkawy |
| 5,263,483 A | 11/1993 | Nishigaki et al. |
| 5,265,613 A | 11/1993 | Feldman et al. |
| 5,268,877 A | 12/1993 | Odell |

(Continued)

FOREIGN PATENT DOCUMENTS

| | | |
|---|---|---|
| CN | 1140982 A | 1/1997 |
| CN | 1361871 A | 7/2002 |

(Continued)

OTHER PUBLICATIONS

PCT Notification of Transmittal of the International Search Report and the Written Opinion of the International Searching Authority, Sep. 30, 2008.

(Continued)

*Primary Examiner* — Long V. Le
*Assistant Examiner* — Angela M Hoffa
(74) *Attorney, Agent, or Firm* — Rutan & Tucker, LLP

(57) ABSTRACT

A low power ultrasound system for use in sonography applications, including vascular imaging, is disclosed. In one embodiment, the low power ultrasound system comprises a base unit that includes an image processor and a display. An ultrasound probe is operably connected to the base unit. The probe includes a head portion including an array of crystal transducers. A plurality of pulser/receiver modules that cause the transducers to emit ultrasonic transmit pulses are also included in the probe. The pulser/receiver modules are further configured to receive analog signals relating to ultrasonic echo receive pulses detected by the transducers. The probe includes a singular low noise amplifier that amplifies the analog signals, and an analog-to-digital converter that converts the analog signals to a digital signal. A wireless interface is included for enabling the digital signal to be wirelessly transmitted from the probe to the image processor of the base unit.

17 Claims, 6 Drawing Sheets

U.S. PATENT DOCUMENTS

| | | | |
|---|---|---|---|
| 5,295,485 A | 3/1994 | Shinomura et al. | |
| 5,295,958 A | 3/1994 | Shturman | |
| 5,345,426 A | 9/1994 | Lipschutz | |
| 5,363,852 A | 11/1994 | Sharkawy | |
| 5,369,624 A | 11/1994 | Fukukita et al. | |
| 5,443,446 A | 8/1995 | Shturman | |
| 5,484,416 A | 1/1996 | Gittings | |
| 5,522,391 A | 6/1996 | Beaudin et al. | |
| 5,544,128 A | 8/1996 | Kim et al. | |
| 5,590,658 A | 1/1997 | Chiang et al. | |
| 5,622,177 A * | 4/1997 | Breimesser et al. | 600/459 |
| 5,640,960 A | 6/1997 | Jones et al. | |
| 5,685,307 A | 11/1997 | Holland et al. | |
| 5,690,114 A | 11/1997 | Chiang et al. | |
| 5,722,412 A | 3/1998 | Pflugrath et al. | |
| 5,782,769 A | 7/1998 | Hwang et al. | |
| 5,817,024 A | 10/1998 | Ogle et al. | |
| 5,865,733 A | 2/1999 | Malinouskas et al. | |
| 5,893,363 A | 4/1999 | Little et al. | |
| 5,964,709 A | 10/1999 | Chiang et al. | |
| 5,997,479 A | 12/1999 | Savord et al. | |
| 6,102,863 A | 8/2000 | Pflugrath et al. | |
| 6,117,085 A | 9/2000 | Picatti et al. | |
| 6,126,608 A | 10/2000 | Kemme et al. | |
| 6,135,958 A | 10/2000 | Mikula-Curtis et al. | |
| 6,135,961 A | 10/2000 | Pflugrath et al. | |
| 6,139,496 A | 10/2000 | Chen et al. | |
| 6,142,946 A | 11/2000 | Hwang et al. | |
| 6,203,498 B1 | 3/2001 | Bunce et al. | |
| 6,213,951 B1 | 4/2001 | Krishnan et al. | |
| 6,248,073 B1 * | 6/2001 | Gilbert et al. | 600/447 |
| 6,251,073 B1 * | 6/2001 | Imran et al. | 600/443 |
| 6,344,024 B1 | 2/2002 | Brucher et al. | |
| 6,375,617 B1 | 4/2002 | Fraser | |
| 6,379,304 B1 | 4/2002 | Gilbert et al. | |
| 6,379,305 B1 | 4/2002 | Eugley | |
| 6,383,139 B1 | 5/2002 | Hwang et al. | |
| 6,416,475 B1 | 7/2002 | Hwang et al. | |
| 6,436,048 B1 | 8/2002 | Pesque | |
| 6,440,072 B1 | 8/2002 | Schuman et al. | |
| 6,468,216 B1 | 10/2002 | Powers et al. | |
| 6,471,651 B1 * | 10/2002 | Hwang et al. | 600/459 |
| 6,475,146 B1 | 11/2002 | Frelburger et al. | |
| 6,478,740 B2 | 11/2002 | Souney et al. | |
| 6,482,158 B2 | 11/2002 | Mault | |
| 6,494,838 B2 | 12/2002 | Cooley et al. | |
| 6,540,682 B1 | 4/2003 | Leavitt et al. | |
| 6,540,685 B1 | 4/2003 | Rhoads et al. | |
| 6,569,101 B2 | 5/2003 | Quistgaard et al. | |
| 6,569,102 B2 * | 5/2003 | Imran et al. | 600/459 |
| 6,575,908 B2 | 6/2003 | Barnes et al. | |
| 6,605,043 B1 | 8/2003 | Dreschel et al. | |
| 6,645,148 B2 | 11/2003 | Nguyen-Dinh et al. | |
| 6,746,402 B2 | 6/2004 | Ustuner | |
| 6,780,154 B2 | 8/2004 | Hunt et al. | |
| 6,783,493 B2 | 8/2004 | Chiang et al. | |
| 6,806,623 B2 * | 10/2004 | Petersen et al. | 310/334 |
| 6,869,401 B2 * | 3/2005 | Gilbert et al. | 600/459 |
| 6,875,178 B2 * | 4/2005 | Phelps et al. | 600/447 |
| 6,936,008 B2 | 8/2005 | Tarakci et al. | |
| 6,962,566 B2 | 11/2005 | Quistgaard et al. | |
| 6,994,674 B2 * | 2/2006 | Sheljaskow et al. | 600/459 |
| 7,115,093 B2 * | 10/2006 | Halmann et al. | 600/437 |
| 7,549,961 B1 | 6/2009 | Hwang | |
| 7,604,596 B2 | 10/2009 | Hwang et al. | |
| 7,691,063 B2 * | 4/2010 | Peteresen et al. | 600/447 |
| 7,789,833 B2 * | 9/2010 | Urbano et al. | 600/439 |
| 7,874,991 B2 * | 1/2011 | Chiang et al. | 600/459 |
| 2002/0016545 A1 | 2/2002 | Quistgaard et al. | |
| 2002/0038088 A1 * | 3/2002 | Imran et al. | 600/443 |
| 2002/0065464 A1 | 5/2002 | Murphy et al. | |
| 2002/0177774 A1 | 11/2002 | Hwang et al. | |
| 2003/0013966 A1 | 1/2003 | Barnes et al. | |
| 2003/0097071 A1 | 5/2003 | Halmann et al. | |
| 2003/0139664 A1 | 7/2003 | Hunt et al. | |
| 2003/0195418 A1 | 10/2003 | Barnes et al. | |
| 2003/0220573 A1 * | 11/2003 | Imran et al. | 600/459 |
| 2003/0236539 A1 | 12/2003 | Rabiner et al. | |
| 2004/0002652 A1 * | 1/2004 | Phelps et al. | 600/437 |
| 2004/0002656 A1 * | 1/2004 | Sheljaskow et al. | 600/459 |
| 2004/0015079 A1 * | 1/2004 | Berger et al. | 600/437 |
| 2004/0158154 A1 | 8/2004 | Hanafy et al. | |
| 2004/0181206 A1 | 9/2004 | Chiu et al. | |
| 2004/0225220 A1 | 11/2004 | Rich | |
| 2005/0057304 A1 | 3/2005 | Gilbert et al. | |
| 2005/0068221 A1 | 3/2005 | Freeman et al. | |
| 2005/0148873 A1 * | 7/2005 | Petersen et al. | 600/447 |
| 2005/0148878 A1 * | 7/2005 | Phelps et al. | 600/459 |
| 2005/0181343 A1 | 8/2005 | Ault et al. | |
| 2005/0203392 A1 * | 9/2005 | Peteresen et al. | 600/437 |
| 2005/0228281 A1 | 10/2005 | Nefos | |
| 2006/0025684 A1 | 2/2006 | Quistgaard et al. | |
| 2006/0036218 A1 | 2/2006 | Goodson et al. | |
| 2006/0064159 A1 | 3/2006 | Porter et al. | |
| 2006/0100568 A1 | 5/2006 | Tan | |
| 2006/0184029 A1 | 8/2006 | Haim et al. | |
| 2006/0224110 A1 | 10/2006 | Scott et al. | |
| 2007/0016068 A1 | 1/2007 | Grunwald et al. | |
| 2007/0161904 A1 * | 7/2007 | Urbano | 600/459 |
| 2007/0232910 A1 | 10/2007 | Hwang et al. | |
| 2007/0239019 A1 * | 10/2007 | Richard et al. | 600/459 |
| 2008/0114239 A1 * | 5/2008 | Randall et al. | 600/437 |
| 2008/0114241 A1 * | 5/2008 | Randall et al. | 600/443 |
| 2008/0114245 A1 * | 5/2008 | Randall et al. | 600/447 |
| 2008/0114246 A1 * | 5/2008 | Randall et al. | 600/447 |
| 2008/0114247 A1 * | 5/2008 | Urbano et al. | 600/447 |
| 2008/0114248 A1 * | 5/2008 | Urbano et al. | 600/447 |
| 2008/0114249 A1 * | 5/2008 | Randall et al. | 600/447 |
| 2008/0114250 A1 * | 5/2008 | Urbano et al. | 600/447 |
| 2008/0114251 A1 * | 5/2008 | Weymer et al. | 600/447 |
| 2008/0114252 A1 * | 5/2008 | Randall et al. | 600/447 |
| 2008/0114253 A1 * | 5/2008 | Randall et al. | 600/459 |
| 2008/0119730 A1 | 5/2008 | Kim et al. | |
| 2008/0119731 A1 | 5/2008 | Becerra et al. | |
| 2008/0119737 A1 * | 5/2008 | Urbano et al. | 600/459 |
| 2008/0125655 A1 | 5/2008 | Song et al. | |
| 2008/0161686 A1 | 7/2008 | Halmann | |
| 2008/0188747 A1 * | 8/2008 | Randall et al. | 600/443 |
| 2008/0188750 A1 * | 8/2008 | Randall et al. | 600/454 |
| 2008/0188752 A1 * | 8/2008 | Randall et al. | 600/455 |
| 2008/0208061 A1 | 8/2008 | Halmann | |
| 2008/0281206 A1 | 11/2008 | Bartlett et al. | |
| 2009/0018443 A1 * | 1/2009 | Colby | 600/437 |
| 2009/0093719 A1 | 4/2009 | Pelissier et al. | |
| 2009/0093720 A1 * | 4/2009 | Petersen et al. | 600/447 |
| 2009/0105587 A1 * | 4/2009 | Petersen et al. | 600/437 |
| 2009/0198132 A1 | 8/2009 | Pelissier et al. | |
| 2010/0286527 A1 * | 11/2010 | Cannon et al. | 600/459 |

FOREIGN PATENT DOCUMENTS

| | | |
|---|---|---|
| EP | 0574923 A2 | 12/1993 |
| EP | 0712294 A1 | 5/1996 |
| EP | 2135110 B1 | 10/2012 |
| JP | 57170230 A | 10/1982 |
| JP | 62227326 A | 10/1987 |
| JP | H02-156933 | 6/1990 |
| JP | 03023853 A | 1/1991 |
| JP | H10-290799 | 11/1998 |
| JP | 2003-506172 A | 2/2003 |
| JP | 2005-168903 A | 6/2005 |
| JP | 2006-20749 | 1/2006 |
| WO | 9217118 A1 | 10/1992 |
| WO | 9504502 A1 | 2/1995 |
| WO | 9512354 A1 | 5/1995 |
| WO | WO-9701768 | 1/1997 |
| WO | 9828631 A2 | 7/1998 |
| WO | WO-0031563 | 6/2000 |
| WO | WO-0079300 | 12/2000 |
| WO | 0152753 A1 | 7/2001 |
| WO | 03072000 A1 | 9/2003 |
| WO | WO-03073940 | 9/2003 |
| WO | 2004032791 A2 | 4/2004 |
| WO | 2004096062 A1 | 11/2004 |
| WO | 2004107965 A2 | 12/2004 |
| WO | 2005043188 A1 | 5/2005 |
| WO | 2005099345 A2 | 10/2005 |
| WO | 2006019848 A1 | 2/2006 |

| WO | 2006026687 A2 | 3/2006 |
| WO | 2006076326 A2 | 7/2006 |
| WO | 2006105008 A1 | 10/2006 |
| WO | 2006105009 A1 | 10/2006 |
| WO | 2006116558 A2 | 11/2006 |
| WO | 2007022133 A1 | 2/2007 |
| WO | 2008124841 A3 | 11/2008 |

OTHER PUBLICATIONS

Timothy Ritter et al., Single Crystal PZN/PT-Polymer Composites for Ultrasound Transducer Applications, Jul. 2000, vol. 47, No. 4, IEEE Xplore.

Butler et al, Practical Considerations for Analog Operation of Bucket-Brigade Circuits, IEEE Journal of Solid-State Circuits, pp. 157-168, vol. 8 No. 2, Apr. 1973.

EP 2008745537.4 filed Apr. 10, 2008 Examiner's Report dated Feb. 8, 2010.

Foster, F.S. et al, A Ditital Annular Array Prototype Scanner for Realtime Ultrasound Imaging, Ultrasound in Med and Biol, pp. 661-672, vol. 15, No. 7, 1989.

Freeman et al, Delta-sigma oversampled Ultrasound Beamformer with Dynamics Delays, IEEE Transactions on Ultrasonics, Ferroeletrics and Frequency Control, pp. 320-332, vol. 46 No. 2, Mar. 1999.

Kassem et al, Perception SoC Based on an Ultrasonic Array of Sensors: Efficient DSP Core Implementation and Subsequent Experimental Results, EURASIP Journal on Applied Signal Processing, pp. 1071-1081, vol. 2005 No. 7, 2005.

Linnenbrink et al, Low-Power, Low-Cost, High-Performance Beamformer for Medical Ultrasound Scanners, from <http://handle.dtic.mil/100.2/ADB215719>, 44 pages, Oct. 1996.

Mo et al, Front-end Processor using BBD distributed Delay-sum Architecture for Micromachined Ultrasonic Sensor Array, Journal of Microelectromechanical Systems, pp. 506-512, vol. 12 No. 4, Aug. 2003.

Mo et al, Integrated Analog Beam Former Based on Bucket Brigade Device for Micromachined Ultrasonic Sensor Array, Shanghai University, Shanghai, China Apr. 22, 2002.

Mo et al, Pipelined delay-sum architecture based on Bucket-brigade Devices for On-chip Ultrasound Beamforming, IEEE Journal of Solid-State Circuits, pp. 1754-1757, vol. 38 No. 10, Oct. 2003.

Mucci et al, A Comparison of Efficient Beamforming Algorithms, IEEE Transactions on Acoustics, Speech and Signal Processing, pp. 548-558, vol. 32 No. 3, Jun. 1984.

PCT/US2008/059940 filed Apr. 10, 2008 International Preliminary Examination on Patentability dated Oct. 13, 2009.

Raffel et al, Practical Modeling of Bucket-Brigade Device Circuits, 7 pages, Proc. of the 13th Int. Conference on Digital Audio Effects (DAFx-10), Graz, Austria , Sep. 6-10, 2010.

Savord, B et al, Fully Sampled Matrix Transducer for Real Time 3D Ultrasonic Imaging, IEEE Symposium on Ultrasonics, pp. 945-953, Oct. 5-8, 2003.

Tanaka et al, Development of Bbd Adding-Delay Architecture for Ultrasonic Micro Array Sensor, IEEJ Transactions on Sensors and Micromachines, pp. 188-195, vol. 125, Issue 4, 2005.

Thomenius K.E., Evolution of Ultrasound Beamformers, Ultrasonics Symposium, 1996, Proceedings, 1996 IEEE, pp. 1615-1622 vol. 2, Nov. 3-6, 1996.

Wygant et al, An Integrated Circuit with Transmit Beamforming Flip-Chip Bonded to a 2-D CMUT Array for 3-D Ultrasound Imaging, IEEE Transactions on Ultrasonics, Ferroelectrics, and Frequency Control, pp. 2145-2156, vol. 56 No. 10, Oct. 2009.

CN 200880017662.2 filed Apr. 10, 2008 First Office Action dated Feb. 1, 2012.

CN 200880017662.2 filed Apr. 10, 2008 Second Office Action dated Nov. 13, 2012.

EP 08745537.4 filed Apr. 10, 2008 Intention to Grant dated May 11, 2012.

EP 12154188.2 filed Apr. 10, 2008 Exam Report dated Dec. 13, 2012.

EP 12154188.2 filed Apr. 10, 2008 Search Report dated Apr. 12, 2012.

JP 2010-503208 filed Apr. 10, 2008 Office Action dated Nov. 22, 2011.

JP 2010-503208 filed Apr. 10, 2008 Office Action dated Nov. 8, 2012.

\* cited by examiner

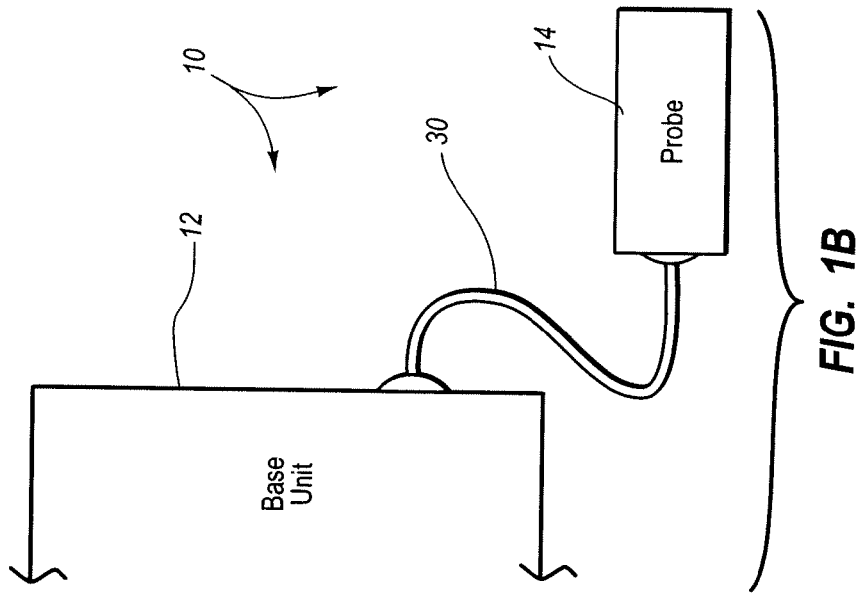
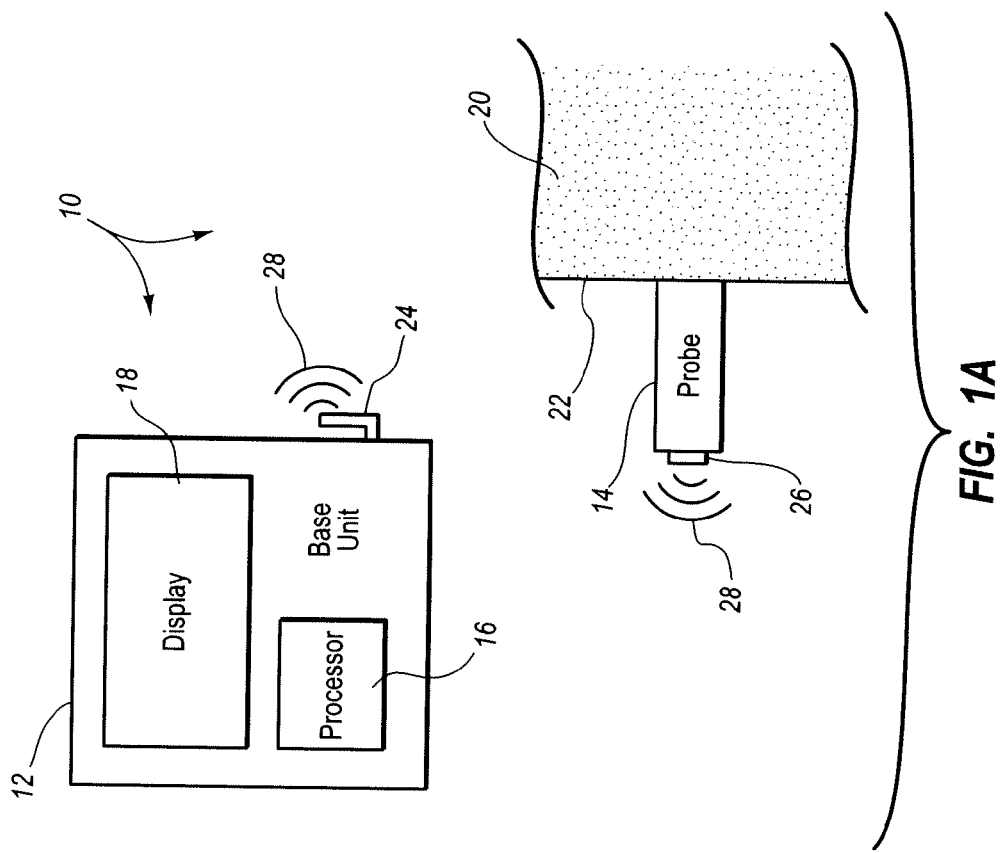

LOW POWER ULTRASOUND SYSTEM

CROSS-REFERENCE TO RELATED APPLICATION

This application claims the benefit of U.S. Provisional Patent Application No. 60/922,695, filed Apr. 10, 2007, and entitled "Low Power, Low Cost Wireless Ultrasound Machine," which is incorporated herein by reference in its entirety.

BRIEF SUMMARY

Briefly summarized, embodiments of the present invention are directed to a low power ultrasound system for use in sonography applications, including vascular imaging. The system to be described requires relatively low power levels in order to function, thereby enabling the system to take advantage of wireless technologies to un-tether the ultrasound probe from the base unit of the system. This, in turn, provides more flexibility for a clinician or other user of the system and simplifies the ultrasonic procedure. Embodiments of the present invention enable the ultrasound device to operate with low power requirements, thereby facilitating wireless connectivity between the probe and base unit and acceptable operating times for the probe between recharging.

In one embodiment, the low power ultrasound system comprises a base unit that includes an image processor and a display. An ultrasound probe is operably connected to the base unit. The probe includes a head portion including an array of crystal transducers. A plurality of pulser/receiver modules, which cause the transducers to emit ultrasonic transmit pulses, are also included in the probe. The transmit pulses are reflected by the object being imaged, causing ultrasonic echo receive pulses that are received by the transducers and forwarded to the corresponding pulser/receiver modules as electrical analog signals. The probe includes a multiplexer that combines the analog signals, a singular low noise amplifier that amplifies the multiplexed analog signals, and an analog-to-digital converter that converts the multiplexed analog signals to a digital signal.

In one embodiment, a wireless interface is included in the ultrasound probe for enabling the digital signal to be wirelessly transmitted from the probe to the image processor of the base unit, which also includes a compatible wireless interface. A processor in the base unit processes the data produces an ultrasonic image. Such wireless connectivity is enabled by the low power configuration of the probe components as described above.

One or more of a variety of wireless protocols may be employed to facilitate communication between the probe and base unit, including a wireless universal serial bus ("USB") protocol. In another embodiment, the probe can be physically cabled to the base unit using a USB interface, for example. The base unit can be a dedicated ultrasound device, a desktop or laptop computer, etc. These and other features of the present invention will become more fully apparent from the following description and appended claims, or may be learned by the practice of embodiments of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1A is a simplified diagram of a low power ultrasound system configured in accordance with one example embodiment of the present invention;

FIG. 1B is a simplified view of a portion of FIG. 1A in accordance with an alternative example embodiment;

DETAILED DESCRIPTION OF SELECTED EMBODIMENTS

Figure 2:
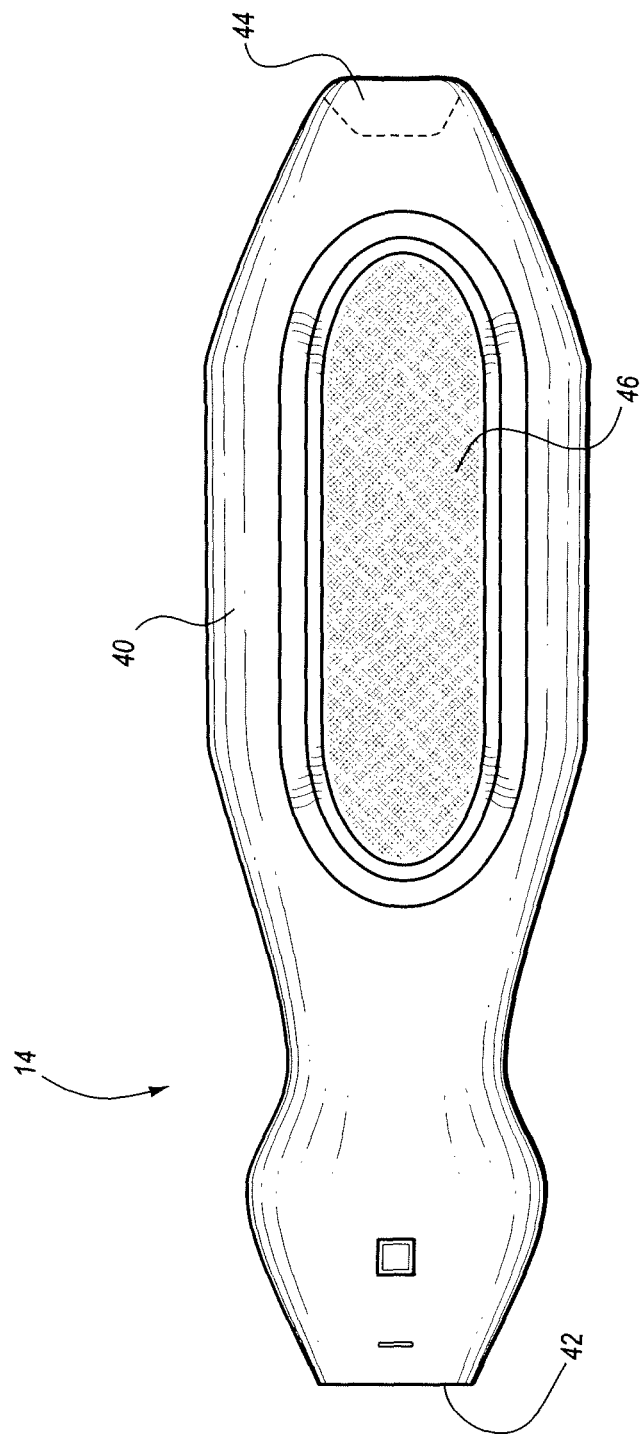
FIG. 2 is a top view of a wireless probe that can be employed in connection with the low power ultrasound system shown in FIG. 1A.

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-6B depict various features of embodiments of the present invention, which embodiments are generally directed to a system for performing ultrasound imaging on the body of a patient or other subject. Advantageously, the system to be described requires relatively low power levels in order to function, thereby enabling the system to take advantage of wireless technologies to un-tether the ultrasound probe from the base unit of the system. This, in turn, provides more flexibility for a clinician or other user of the system and simplifies the ultrasonic procedure.

Reference is first made to FIG. 1A, which shows a low power ultrasound system, generally designated at 10, configured in accordance with one example embodiment of the present invention. As shown, the low power ultrasound system ("system") 10 generally includes a base unit 12 and probe 14. The base unit 12 as pictured here includes a processor 16 for performing image processing functions on sonographic data retrieved by the probe 14 during an ultrasonic procedure. FIG. 1A shows the probe 14 placed adjacent a surface 22 of a body 20 of a patient or other subject. Though understood to be used in applications such as that shown here in FIG. 1A, it is also appreciated that embodiments of the present invention may be modified for use with probes having other shapes and configurations, including probes configured for penetration into an orifice of the patient, for instance.

The base unit 12 further includes a display 18. Image data processed by the processor 16 of the base unit 12 are represented as an image on the display 18. The image is continually refreshed during operation of the system 10. Note that, for clarity, only selected features of the base unit 12, probe 14, and the system 10 are described herein in detail. Indeed, it is appreciated that the system 10 and its individual components can include additional features and components, though not disclosed herein, while still preserving the principles of the present invention. Note also that the base unit 12 can be one of any number devices, including a dedicated ultrasound device, a desktop or laptop computer, etc.

In the presently depicted embodiment, the system 10 implements wireless technology, wherein the base unit 12 and the probe 14 are in two-way, wireless communication with one another. To that end, the base unit 12 includes a base antenna 24 that wireless communicates with a probe antenna 26 included with the probe 14. Wireless signals 28, representing electromagnetic communication such as RF signals between the base unit 12 and the probe 14, are also shown. In this way, sonographic data detected by the probe 14 can be wirelessly transmitted by the probe antenna 26 to the base unit 12 via the base antenna 24 for processing by the processor 16. Note that one or more of a variety of wireless data transfer protocols, including Wireless USB, IEEE 802.x, BLUETOOTH, WIMAX, etc., may be employed for such data transfer as described herein.

FIG. 1B represents another possible embodiment, wherein the base unit 12 of the low power ultrasound system 10 is communicatively coupled with the probe 14 not wirelessly, but via a cable 30. As such, it is appreciated that the low power ultrasound system as described herein may be employed with a wireless, non-wireless, or even hybrid wireless/cabled communication link between the base unit and the probe.

Reference is now made to FIG. 2, which depicts various details regarding the probe 14 of the system 10 shown in FIG. 1A. As depicted, the probe 14 according to the present embodiment is a wireless probe and includes a probe housing that acts as a covering for various internal components of the probe. A head 42 is included in the probe 14 and houses the array of crystals that act as transducers to enable insonation of an object within the body of the patient to be imaged during ultrasound procedures. A location 44 is specified, depicting one possible location for inclusion of an internal probe antenna enabling wireless communication with the base unit 12 as generally depicted in FIG. 1A.

A location 46 is also designated for the inclusion of various buttons (not shown) that enable clinician control of the probe 14 and the base unit 12 during ultrasound procedures. Thus, it is appreciated that the probe 14 as shown in FIG. 2 can be desirably included within the sterile field of a patient undergoing an ultrasound procedure in preparation for receiving an intravenous catheter, such as a PICC line, for instance. Note that the particular design of the probe 14 as shown in FIG. 2, together with the specified location for the various components thereof—both internal and external—can be varied such that the size, look, and configuration of the probe may be modified from what is explicitly shown here.

Figure 3:
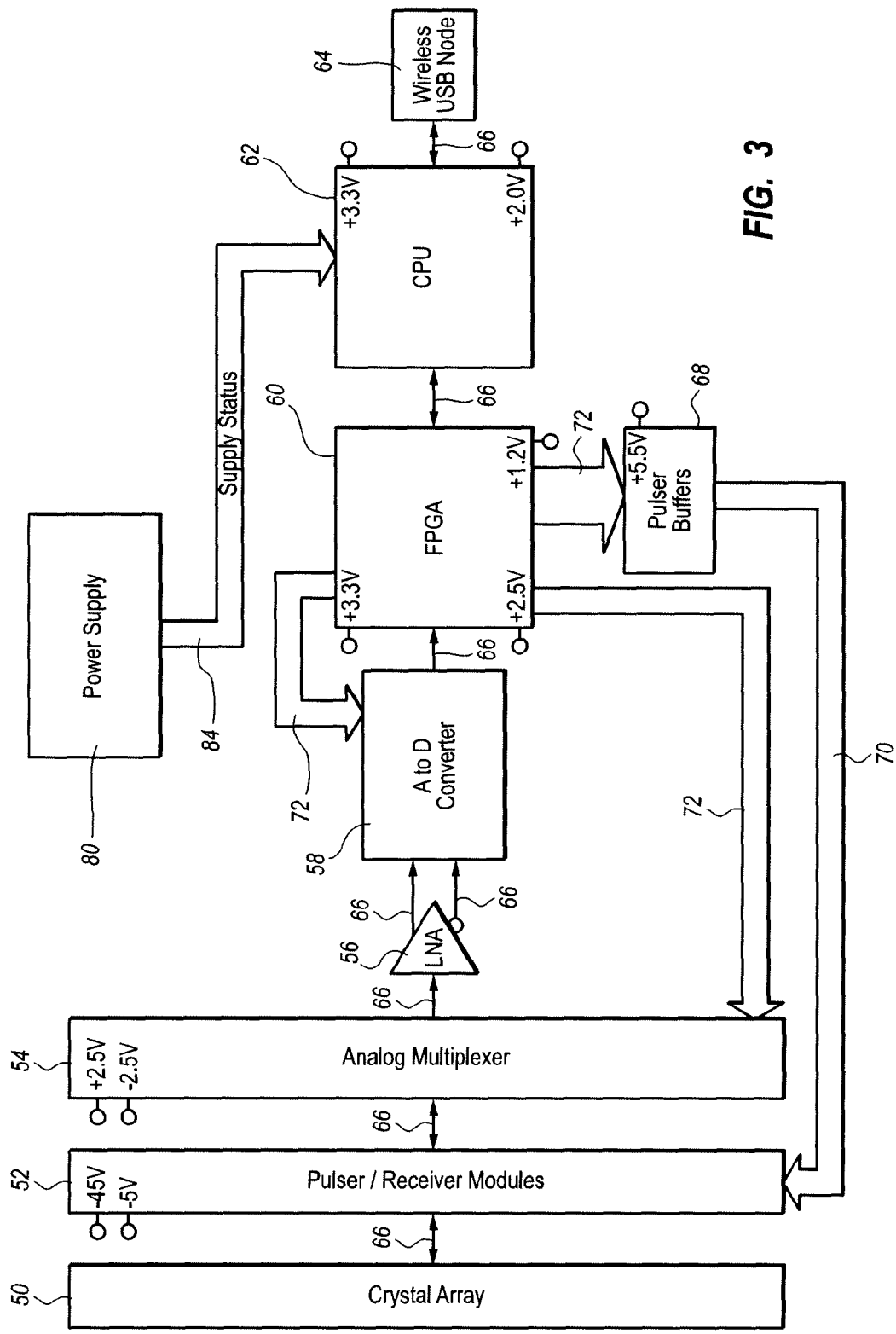
FIG. 3 is a simplified block diagram of internal components of the ultrasound probe shown in FIG. 2.

Reference is now made to FIG. 3 in describing various internal components included in the probe 14 of the system 10, according to one embodiment. In doing so, it should be appreciated that the layout and configuration of the components in FIG. 3, shown in simplified form, enable the system 10 to operate in a low power configuration. The low power requirements of the components of the probe 14 shown in FIG. 3 enable various advantages to be realized, including the ability for the probe to operate wirelessly with respect to the base unit 12 while still having a suitable operating time between recharging. Note that, though shown here as singular, the components to be described in connection with FIG. 3 can be configured as a single device or multiple devices, as may be appreciated by one skilled in the art.

In greater detail, FIG. 3 shows that the probe 14 internally includes a crystal array 50, each crystal of the array functioning as a piezoelectric transducer. The crystal array 50 here includes 64 crystals and is located in the head 42 (FIG. 2) of the Probe 14 and is linearly arranged in the present embodiment. In other embodiments, both the number and arrangement of the crystals can vary.

One or more pulser/receiver modules 52 are operably connected to the crystal array 50 and are configured to drive one or more active crystals in the crystal array 50 during operation of the system 10 so as to cause the respective crystal to produce a transmit pulse of ultrasonic waves, well known in the art. The pulser/receiver modules 52 are also configured to receive electrical pulses representing received echo pulses detected by the active crystals of the crystal array 50, wherein the echo pulses are produced as a result of reflection of the transmit pulses by an object to be imaged within the patient body, such as a vein or artery.

A signal line 66 is shown interposed between various of the components depicted in FIG. 3, including the crystal array 50, the pulser/receiver modules 52, etc. Note that the signal line 66 is representative of one or more signal paths on which signals associated with ultrasonic echo receive pulses are carried between the internal probe components described herein. As such, the signal line 66 may take one or more of several forms between the various internal probe components, as known by one skilled in the art.

An analog multiplexer 54 is operably connected to the pulser/receiver modules 52 and is configured to multiplex multiple electrical pulses representing the received echo pulses forwarded by the pulser/receiver modules. The multiplexer 54 in the present embodiment is a composite configuration of eight "1-of-8" multiplexers, each of which is operably connected to a corresponding plurality of eight pulser/receiver modules 52 (see FIGS. 4A, 4B). The composite multiplexer 54 is operably connected to a field-programmable gate array (or "FPGA," described below at 60) having 3 binary-decoded select lines and 8 enable lines to the eight multiplexers to enable the signals from one multiplexer at a time to be forwarded along the signal line 66. Of course, other multiplexer configurations, including a different number of individual multiplexers included in the composite multiplexer, can be employed.

A single low-noise amplifier ("LNA") 56 is operably connected to the multiplexer 54 and is configured to amplify the multiplexed signal received from the multiplexer. Note that the LNA 56 receives a single-ended analog signal from the multiplexer 54 and, in addition to amplifying it, produces for output a differential analog signal. This differential analog signal is forwarded to a single analog-to-digital converter ("ADC") 58, which converts it to a digital signal. The ADC 58 is a 16-bit ADC in one embodiment, such as part number LTC2203CUK or LTC2203IUK, sold by Linear Technology, 1630 McCarthy Blvd., Milpitas, Calif., 95035-7417.

Note that only a single LNA and a single ADC are used in the present embodiment in contrast to other systems, where multiple amplifiers and ADCs are used to simultaneously process converted echo pulses simultaneously received by the crystal array. In contrast, the components of the present probe 14 are configured such that only a single signal is amplified by a single amplifier, i.e., the LNA 56, and converted by a single ADC, i.e., the ADC 58, then forwarded for more processing. In this way, the probe 14 has a reduced size, reduced complexity, and lower power consumption when compared to other, known ultrasound systems.

The digital signal produced by the ADC 58, ultimately representing the echo pulses received by the crystal array 50, is then forwarded by the ADC 58 to a field programmable gate array ("FPGA") 60 and a central processing unit ("CPU") 62 before the signal is transmitted to the base unit 12 via a wireless node 64. In one embodiment the CPU 62 is NXP part number LPC2888FET180-S, sold by Royal Philips Electronics, and is employed to govern the FPGA 60 and communication interfaces, such as a wireless node 64 to be described below.

Though specified here as a USB-type wireless node, other node types may be alternatively or additionally employed, as already discussed. For instance, the wireless node 64 could include both Wireless USB and BLUETOOTH wireless data transfer protocols for the wireless transfer of signals from the probe 14 to the base unit 12. Also, and as already mentioned, the wireless nodes can be omitted in one embodiment in favor of a cabled interface between the base unit and the probe. Indeed, in one embodiment, the base unit and probe can be connected via a USB cable. In such a case, the power requirements of the internal components of the probe could be met by the power supply provided by one or more USB outlets of the base unit, if desired, or by a combination of battery and USB-provided power.

As already mentioned, the base unit 12 in the embodiment shown in FIG. 1A, is configured for wireless communication with the wireless probe 14. As such, the base unit 12 wirelessly receives the digital signal that is produced and forwarded via the wireless node 64 as described immediately above. The processor 16 then processes the digital signal according to standard image processing procedures and produces an image that is sent to the display 18 for viewing.

FIG. 3 shows that the probe 14 includes other internal components related to its operation. A plurality of pulser buffers 68 are included and operably connected to the pulser/receiver modules 52 via one or more communication lines 70. The pulser buffers 68 are governed by the FPGA 60 via a communication line 72, which includes in one embodiment 64 signal lines and one enable/disable line, according to the inclusion of 64 transducers in the crystal array 50. So configured, the FPGA 60 assists in activating the proper number of pulser/receiver modules 52 during operation of the device 10.

In addition to the communication line to the pulser buffers 68, communication lines 72 extend from the FPGA 60 to the ADC 58 and the multiplexer 54 to enable the FPGA 60 to govern their operation as well.

A power supply 80 is included in the probe 14 to power the components already described above in connection with FIG. 3. In one embodiment, the power supply 80 is a rechargeable lithium-ion-type battery, though other battery types or alternative power supplies may also be used. A supply status line extends between the power supply 80 and the CPU 62 so as to enable the CPU to monitor battery voltage and to enable the CPU to detect any power supply malfunctions. In other embodiments, one or more smart batteries may alternatively be used.

Various of the components shown in FIG. 3 list voltage values at their corresponding nodes. Note that these voltage values can vary according to the particular configuration of the device(s). It is therefore appreciated that these voltage values are exemplary only, and should not be construed as limiting the present invention in any way.

Figure 4A:
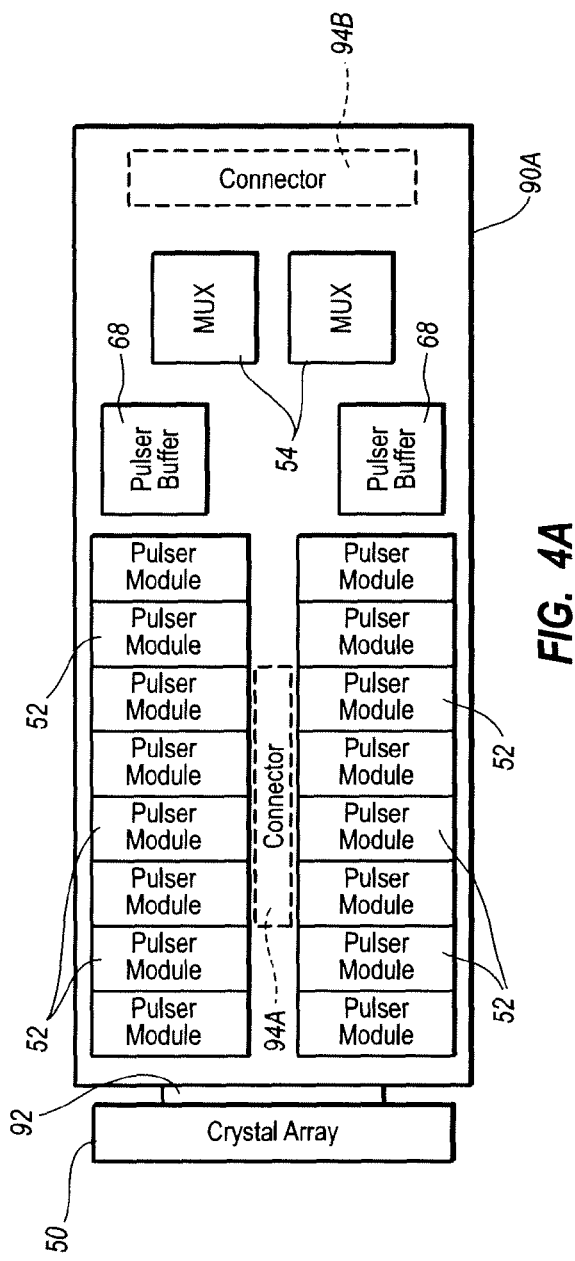
FIG. 4A is a top simplified view of one possible implementation of the components of the ultrasound probe shown in FIG. 3 according to one embodiment.
Figure 4B:
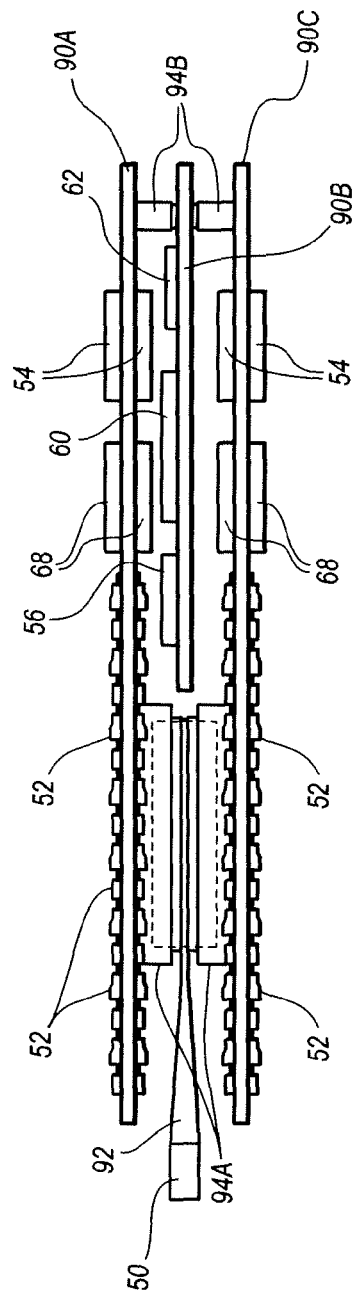
FIG. 4B is a simplified side view of the components of the ultrasound probe shown in FIG. 4A.

Reference is now made to FIGS. 4A and 4B, which depict one possible configuration for arrangement of the various internal components of the probe 14. In particular, these figures show the linear crystal array 50 connected to a top printed circuit board ("PCB") 90 via a flex circuit 92. The plurality of pulser/receiver modules 52 are arranged on top and bottom surfaces of the top PCB 90A and a bottom PCB 90C as well, totaling 64 pulser/receiver modules in the present embodiment, though this number can change according to the particular application. Two pulser buffers 68 are arranged on the top and bottom surfaces of the top PCB 90A and the bottom PCB 90C. Similarly, two multiplexers 54 are arranged on the top and bottom surfaces of the top PCB 90A and the bottom PCB 90C. Connectors 94A are included to interconnect the top and bottom PCBs 90A and 90C to each other and to the flex circuit 92. Connectors 94B are included to interconnect the top and bottom PCBs 90A and 90C with a middle PCB 90B.

The middle PCB 90B includes LNA 56, the FPGA 60, and the CPU 62, together with other probe components, which have been removed for the sake of clarity. The three PCBs 90A-90C are arranged in a stacked "clamshell" design, best seen in FIG. 4B, thereby providing an efficient use of space so as to minimize the size of the probe 14. In one embodiment, for example, the size of the probe 14 is approximately 1.5 inches wide, 3.5 inches long, and 0.5 inch high.

Reference is now made to FIGS. 5A-6B, which depict various operational aspects of the probe 14 during operation of the system 10 to ultrasonically image an object 102, such as a vein, artery, or other feature in the body of a patient. A portion 100 is shown of the crystal array 50 (FIGS. 4A, 4B), including individually numbered crystal transducers 1-34. As mentioned, in the present embodiment, the crystal array of which the portion 100 is a part, includes 64 crystal transducers linearly arranged in the manner shown in FIG. 5A, though both the number and arrangement of the crystal transducers can vary from what is shown here.

Figure 5A:
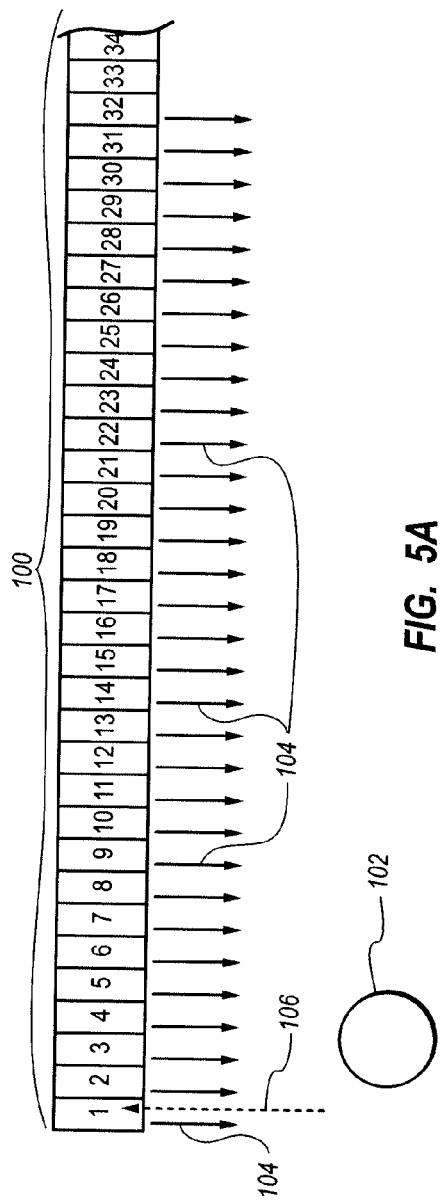
FIG. 5A is a simplified view of a transducer array in a head portion of the ultrasound probe shown in FIGS. 1A and 1B, showing one stage of operation of the transducer array according to one example embodiment.
Figure 5B:
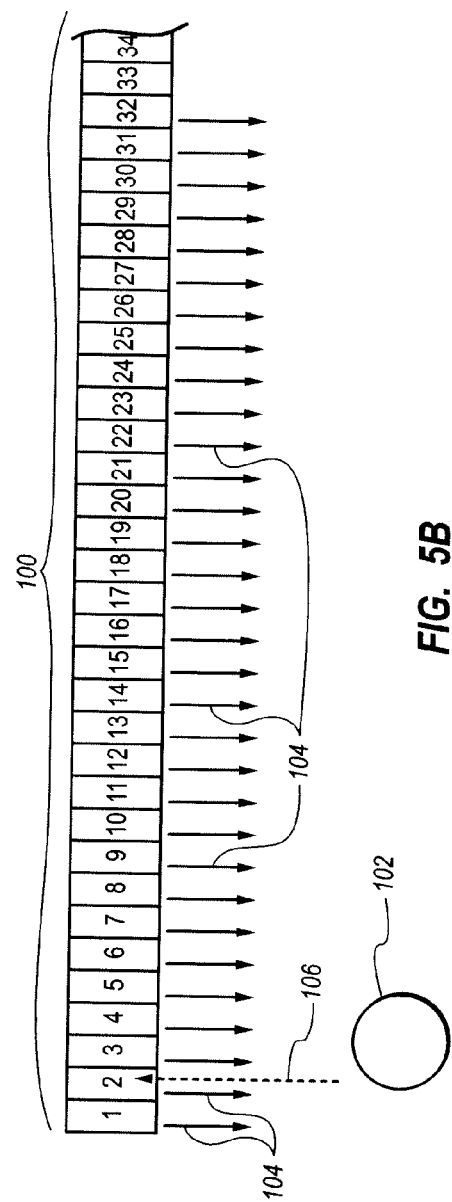
FIG. 5B is a simplified view of the transducer array of FIG. 5A, showing a subsequent stage of operation of the transducer array.
Figure 6A:
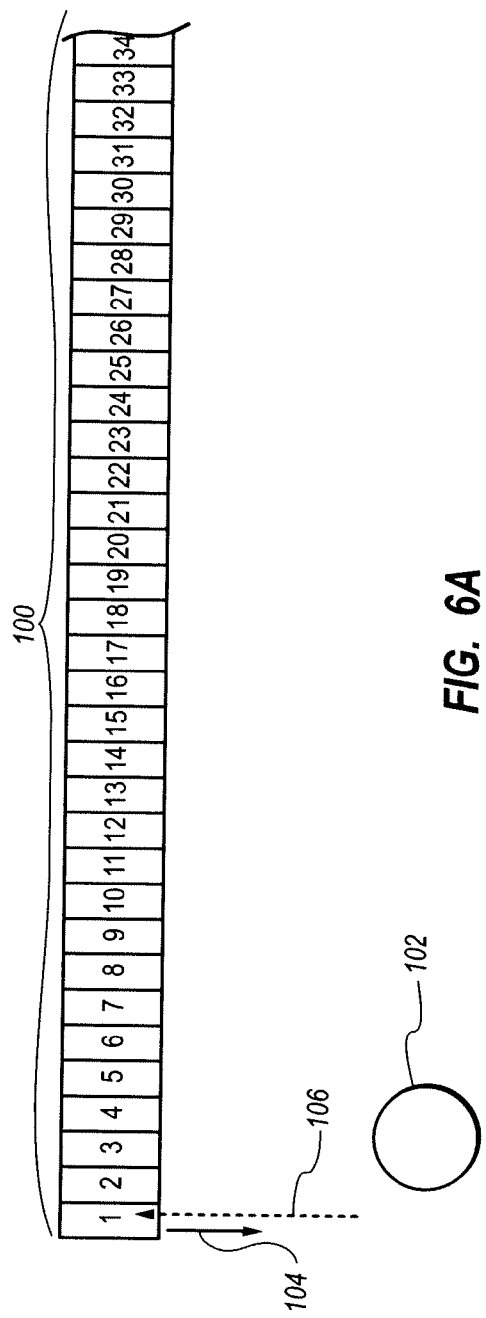
FIG. 6A is a simplified view of the transducer array of FIG. 5A, showing one stage of operation of the transducer array according to another example embodiment.
Figure 6B:
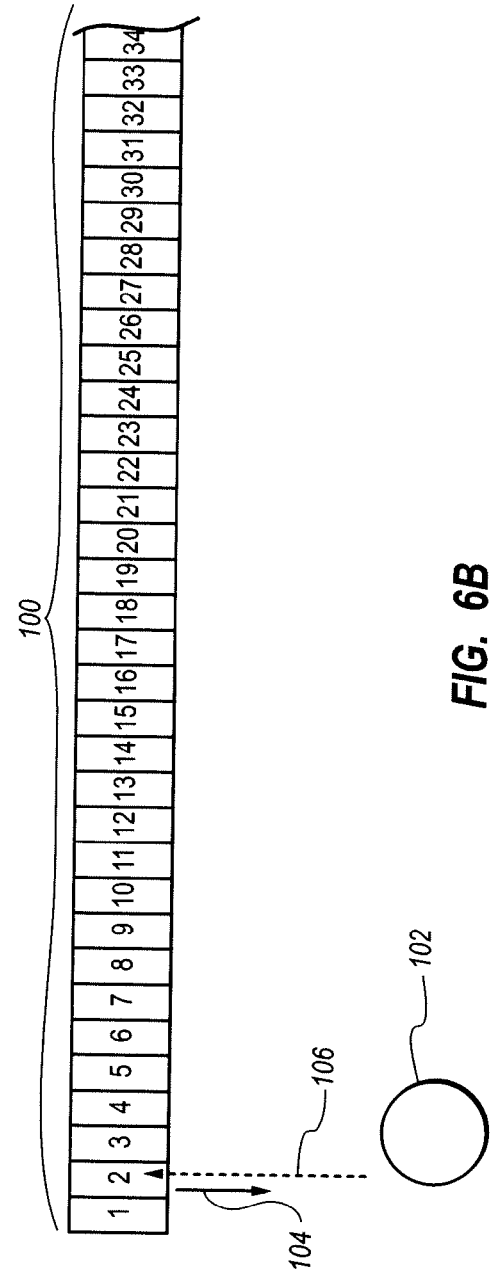
FIG. 6B is a simplified view of the transducer array of FIG. 5A, showing a subsequent stage of operation of the transducer array.

Because the system 10 and probe 14 operate with low power, sonographic scanning techniques are described herein in connection with FIGS. 5A-6B so as to enable ultrasonic imaging while preserving the low power status of the system. FIGS. 5A and 5B depict one such technique. FIGS. 6A and 6B describe another technique. It is appreciated that either of these techniques, or some other technique that is different than, or an amalgam of, the techniques described herein, may be used to produce ultrasonic images using the system 10.

In FIG. 5A, a plurality of ultrasonic transmit pulses 104 are emitted from 32 contiguous transducers, for example, of the crystal array portion 100 toward the object 102 to be imaged. Note that the number of transducers used in any imaging procedure may be more or less than 32 can vary according to many factors, including the size and position of the object to be imaged, etc. In one scanning procedure 10 transducers may be used, in another all the transducers in the array (e.g., 64 in the current embodiments) may be used. Transducer 1 of the array alone is then activated so as to be able to receive and detect an ultrasonic echo receive pulse 106 produced by partial reflection by the object 102 of one or more of the transmit pulses 104. The receive pulse 106 is transmitted through the system in the manner described in connection with FIG. 3.

FIG. 5B shows a subsequent stage of the technique, where a new round of ultrasonic transmit pulses 104 are sent a point in time after, e.g., in rapid succession to, the transmit pulses shown in FIG. 5A. Then, transducer 2 of the array alone is then activated so as to be able to receive and detect a subsequent ultrasonic echo receive pulse 106 produced by partial reflection by the object 102 of one or more of the transmit pulses 104. This subsequent receive pulse 106 is transmitted through the system in the manner described in connection with FIG. 3.

The above process is repeated while advancing the lone active receiving transducer by one through the series of transmitting transducers in order to shape and focus the resulting image of the insonated object 102. In the illustrated embodiment, this signifies cycling the receiving transducer function through all of the transmitting transducers, though this number can be varied if desired or needed for a particular application. In other embodiments, the number of active transducers used to send transmit pulses, the number of transducers receiving an echo pulse at one time, the pattern of activation of the receiving transducers, etc., can be varied.

FIGS. 6A and 6B show another possible ultrasonic scanning technique. In this technique, a single crystal transducer, e.g., crystal 1 alone in the illustrated example, is activated to emit an ultrasonic transmit pulse toward the object 102 to be imaged. Crystal 1 is kept active to receive the echo receive pulse 106 reflected by the object 102. The detected signal is forwarded through the probe 14 to the base unit 12 as has been described in connection with FIG. 3.

The above process is repeated with crystal 2 as the lone active crystal as shown in FIG. 6B, then crystal 3, etc., until each transducer in the selected portion 100 has been utilized. The resulting signals as received by the base unit are processed by the processor 16 to form a shaped and focused ultrasound image of the insonated object 102. As mentioned before, variations of the techniques described in FIGS. 5A-6B can be employed while still falling within the claims of the present invention.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A low power ultrasound imaging device, comprising:
    a base unit including an image processor and a display;
    an ultrasound probe operably connected to the base unit, the probe including:
        a head portion including a crystal transducer array;
        a plurality of pulser/receiver modules that cause the transducer array to emit a plurality of ultrasonic transmit pulses, the pulser/receiver modules configured to receive analog signals relating to ultrasonic echo receive pulses detected by the transducer array;
        a single low noise amplifier that amplifies the analog signals;
        a single analog-to-digital converter that converts the analog signals to a digital signal;
        a processing unit that controls the pulser/receiver modules and the analog-to-digital converter, the pulser/receiver modules causing the transducer array to fire and re-fire the plurality of transducers at the target object and to receive data by only one transducer of the plurality of transducers sequentially until the target object is scanned; and
        an interface for enabling the digital signal to be transferred from the ultrasound probe to the image processor of the base unit.

2. The low power ultrasound imaging device as defined in claim 1, wherein the ultrasound probe further comprises a multiplexer that combines the analog signals before the analog signals are amplified by the low noise amplifier.

3. The low power ultrasound imaging device as defined in claim 1, wherein the ultrasound probe includes a battery for providing power to components of the ultrasound probe.

4. The low power ultrasound imaging device as defined in claim 3, wherein the interface is a wireless interface, and wherein the base unit includes a wireless interface.

5. The low power ultrasound imaging device as defined in claim 4, wherein the wireless interface of the ultrasound probe and the base unit communicate via a wireless data transfer protocol.

6. The low power ultrasound imaging device as defined in claim 1, wherein the interface includes a cable interface between the ultrasound probe and the base unit.

7. The low power ultrasound imaging device as defined in claim 1, wherein the low noise amplifier produces a differential output of amplified analog signals.

8. The low power ultrasound imaging device as defined in claim 1, wherein the ultrasound probe processing unit controls a field-programmable gate array and the interface of the ultrasound probe.

9. The low power ultrasound imaging device as defined in claim 1, wherein the base unit is a laptop computer.

10. A low power ultrasound probe for use in wirelessly transmitting ultrasonic image data to a base unit for production of an ultrasonic image, the low power ultrasound probe comprising:
    an outer covering housing a plurality internal probe components, the internal probe components including:
        a head portion including a plurality of transducers;
        a plurality of pulser/receiver modules that cause the transducers to emit a plurality of ultrasonic transmit pulses, the pulser/receiver modules further configured to receive analog signals relating to a plurality of ultrasonic echo receive pulses detected by at least one of the transducers;
        a multiplexer that combines the analog signals into a multiplexed analog signal;
        a single low noise amplifier that amplifies the multiplexed analog signal;
        a single analog-to-digital converter that converts the multiplexed analog signal to a digital signal;
        a processing unit that controls the pulser/receiver modules and the analog-to-digital converter, the pulser/receiver modules causing the transducer array to fire and re-fire the plurality of transducers at the target object and to receive data by only one transducer of the plurality of transducers sequentially until the target object is scanned; and
        a wireless interface enabling the digital signal to be wirelessly transmitted from the low power ultrasound probe to an image processor of the base unit.

11. An ultrasound probe system comprising:
    the low power ultrasound probe as defined in claim 10; and
    a base unit including a wireless interface for receiving the digital signal transmitted from the ultrasound probe.

12. The low power ultrasound probe as defined in claim 11, wherein the internal probe components are included on at least one circuit board.

13. The low power ultrasound probe as defined in claim 12, wherein the internal probe components are included on three circuit boards, the circuit boards being in a stacked configuration.

14. The low power ultrasound probe as defined in claim 13, wherein the multiplexer includes a plurality of multiplexers that are controlled by a field-programmable gate array.

15. The low power ultrasound probe as defined in claim 14, wherein the plurality of transducers includes 64 crystal transducers, wherein the plurality of pulser/receiver modules includes 64 pulser/receiver modules, and wherein the plurality of multiplexers includes eight multiplexers.

16. The low power ultrasound probe as defined in claim 15, further comprising a lithium-ion battery for powering the internal probe components.

17. The low power ultrasound probe as defined in claim 15, further comprising a plurality of pulser buffers interposed between the field-programmable gate array and the plurality of pulser/receiver modules.

* * * * *